United States Patent [19]

Bisconte

[11] Patent Number: 4,883,642

[45] Date of Patent: Nov. 28, 1989

[54] MEANS TO AUTOMATICALLY HOLD, PROCESS, STORE AND ANALYZE BIOLOGICAL SAMPLES

[75] Inventor: Jean-Claude Bisconte, Vaucresson, France

[73] Assignee: Universite Paris-Nord, Villetaneuse, France

[21] Appl. No.: 865,736

[22] PCT Filed: Jun. 4, 1985

[86] PCT No.: PCT/FR85/00138

§ 371 Date: Sep. 11, 1986

§ 102(e) Date: Sep. 11, 1986

[87] PCT Pub. No.: WO85/05563

PCT Pub. Date: Dec. 19, 1985

[30] Foreign Application Priority Data

Jun. 5, 1984 [FR] France ................................ 84 08769

[51] Int. Cl.⁴ .............................................. G01N 35/02
[52] U.S. Cl. .......................................... 422/66; 422/73; 422/102; 436/46
[58] Field of Search ................................ 422/63–67, 422/73, 102; 436/46

[56] References Cited

U.S. PATENT DOCUMENTS

| | | | |
|---|---|---|---|
| 3,464,799 | 9/1969 | Kimbell | 436/44 |
| 3,497,320 | 2/1970 | Blackburn | 422/66 |
| 3,526,480 | 9/1970 | Findl | 422/66 |
| 3,619,024 | 11/1971 | Frattarola . | |
| 3,620,678 | 11/1971 | Guigan | 422/66 |
| 3,728,081 | 4/1973 | Bidenset . | |
| 4,071,315 | 1/1978 | Chateau | 422/66 |
| 4,218,421 | 8/1980 | Mack, Jr. | 422/66 |

FOREIGN PATENT DOCUMENTS

| | | |
|---|---|---|
| 1900808 | 8/1970 | Fed. Rep. of Germany . |
| 3230901 | 3/1983 | Fed. Rep. of Germany ........ 422/66 |
| 54-51883 | 4/1977 | Japan . |

Primary Examiner—Michael S. Marcus
Attorney, Agent, or Firm—Browdy and Neimark

[57] ABSTRACT

The present invention provides a flexible and transparent ribbon having two continuous longitudinal shoulders disposed along the edges of a face of the ribbon opposite that which is intended to support a plurality of samples to be processed. These shoulders are intended for magnetic, optical, computer or other coding for providing very accurate location, on the order of 10 microns, of elementary sample portions. A space is provided between the shoulders for containing by capillarity a film of appropriate (reactive, rinsing, etc. . . ) liquid. This ribbon may also be provided with microwells and is intended to be contained in a cassette of the type used for video tape recording purposes, having jaws and connected to an image acquisition device and to a microprocessor for control purposes and data processing.

8 Claims, 3 Drawing Sheets

MEANS TO AUTOMATICALLY HOLD, PROCESS, STORE AND ANALYZE BIOLOGICAL SAMPLES

BACKGROUND OF THE INVENTION

1. Field of the Invention

The present invention relates to means for holding, treating, storing and analyzing fixed or living biological samples automatically and continuously.

The analysis of biological samples, such as blood or epithelial smears, histological sections or bacterial cultures, requires sequential phases which often result in observation under a microscope. In most cases, the conventional carrier formed by glass slides is used on which the samples to be analyzed are placed. After different operations, such as fixing and coloring, a thin glass plate is placed on the sample. This process is complex and difficult to automate. It has proved inadequate with respect to the capacities of automatic image analyzers whose use is more and more widespread in medical analysis laboratory practice.

2. Description of the Prior Art

For replacing the rigid and individual glass slides, several authors have proposed using a transparent flexible carrier.

Thus R. D. Mackenzie describes in "Journal of Medical Laboratory Technology", 1962, Volume 19, page 184, the preparation of blood smears using a strip of transparent plastic material.

The British Pat. No. 1 036 776 describes an apparatus and a process for applying biological samples on a transparent carrier ribbon for microscopic analysis, which apparatus comprises two reels for storing and unrolling the ribbon, one of which is contained in a fixing tray, a device for applying the samples on the ribbon, a means for mechanically locating the samples by perforating the ribbon, as well as a possible transparent film for protecting the samples placed on the ribbon wound on itself.

Furthermore, this document suggests the possibility of causing this apparatus to cooperate with a series of successive treatment trays, containing more especially the dyeing and rinsing liquids.

However, the apparatus of said British patent has never been constructed in practice on an industrial scale because the fixing, drying, rinsing, or dyeing times are very different from each other and may vary from a few minutes to several hours, which makes the known devices unsuitable for carrying out a treatment and microscopic analysis which are truly continuous.

The British patent application Nos. 24 304/73, 28 923/73 and 14 494/76, as well as the U.S. Pat. Nos. 471 072 and 589 483 also relate to this technique.

The general concept on which all the above mentioned techniques are based is the use of a transparent ribbon serving as collecting carrier for smears which are applied automatically while the ribbon is travelling past. Although the idea is attractive, it comes up more particularly against said difficulties, which explains that the glass slide still remains widely used whereas substitute methods are making their appearance.

Thus Technicon, with however numerous patents concerning the flexible ribbon concept, has chosen the discontinuous liquid flow system for establishing the blood formula. Other apparatus, such as counters and liquid flow cytometers, may claim to solve certain examinations. Such liquid flow systems, very complex and bulky, have two major drawbacks:

it is not possible to check the results of these automatic devices by a visual morphological examination, nor is it possible to archive the preparations;

the discontinuous flow or cytometry do not allow adaptation to be readily made to small examination flow rates or which vary a great deal because more particularly of high equipment cost.

Moreover, these liquid flow systems are totally unsuitable for the analysis of histological sections, biopsies and for bacteriological examination.

The purpose of the present invention is therefore to provide means for holding, treating, storing and analyzing fixed or living biological samples, automatically and continuously, by making some improvements to previously known flexible and transparent ribbons, by which in particular:

a very accurate topographical location may be obtained, within 10 $\mu$m, of remarkable events formed for example by suspect cells;

multiplication of the reaction times is avoided for the number of samples placed on the ribbon, since each reaction may take place simultaneously for all the samples on the ribbon;

the analysis, more especially microscopic analysis, of living biological samples may be carried out, in particular bacteriological analysis, while taking into account the incubation times of the dividing cells.

SUMMARY OF THE INVENTION

The present invention provides a flexible and transparent ribbon for carrying biological samples and possibly coated with a self adhesive film also transparent for protecting the samples, characterized in that it is provided with two continuous longitudinal shoulders which are disposed along the edges of the face of the ribbon opposite the face intended to carry said samples and which are intended for data storage, such as magnetic, optical, computer or other coding, more especially for the very accurate topographical location of elementary sample portions, as well as for defining a central protection and possibly treatment space for said biological samples by means of a liquid film of appropriate nature, more especially a reaction, rinsing or other film, adhering by capillarity to both faces of the ribbon, this latter being more especially made from a non hydrophobic polymer and filling this space when the ribbon, after being immersed in a bath of said liquid, more especially in a reactive, rinsing or other bath, is then rolled on itself.

In an advantageous embodiment of the ribbon in accordance with the invention, the two shoulders are made from a polymer, in particular identical to the one from which the ribbon is formed.

In a preferred embodiment of the ribbon in accordance with the invention, the two shoulders are made from a magnetic material and form two lateral tracks intended not only for coding the biological samples to be analyzed but also for information storage, for this purpose each lateral track being subdividable into several secondary tracks whose number depends on the complexity of the analysis and on the information to be stored.

In another advantageous embodiment of the ribbon of the invention, it comprises a plurality of rows of microwells disposed perpendicularly to the longitudinal axis of the ribbon except in correspondance with the position of said lateral shoulders.

Whereas the embodiment of the smooth ribbon is suitable for fixed biological sample analysis, the embodiment of the micro-well ribbon is suitable for the analysis of living biological samples, more especially for bacteriological analysis.

In a preferred arrangement of this embodiment the micro-wells are formed integrally with the ribbon by molding.

In an advantageous feature of this arrangement, the micro-wells are polyhedral.

In an advantageous variant of this feature the micro-wells are cylindrical.

In an advantageous variant of this embodiment, said ribbon carries micro-wells formed by toroidal rings which are fixed, by bonding or similar, to a smooth ribbon and said shoulders have an increased height so that said space formed therebetween contains the micro-wells thus formed.

In an advantageous arrangement of this embodiment and of its variant, said film for protecting the biological samples is permeable or impermeable to air, depending on whether it is desired for the reactions inside said micro-wells to take place under aerobic or anaerobic conditions.

In accordance with the invention, in the case where the micro-wells are obtained by molding, pads impregnated with an appropriate lyophilized product, more especially a substrate, a dye or other, are applied to the face of said micro-well protection film which adheres to the ribbon, and the face of each pad which is turned towards the bottom of the corresponding micro-well is coated with silver for reflecting the incident light coming from an appropriate optical device, more particularly an optical fiber device, a second adhesive film protecting said lyophilized product pads.

Also in accordance with the invention, in the case where the micro-wells are obtained by application of toroidal rings on a smooth ribbon, said lyophilized product pads are disposed on the bottom of each micro-well and are partially housed in recesses formed at the base of each ring so as to be held in position by compression between each ring and the ribbon.

In a preferred variant of this arrangement, said lyophilized product is housed in a circular groove, continuous or not, formed in the internal wall of said toroidal rings, so that release of the lyophilized product is provided by crushing the micro-wells.

The present invention also provides a device for storing and feeding the carrier ribbon according to any one of the above arrangements, characterized in that it is formed by a cassette substantially of the type used in video tape recording and comprising, in particular, two spools known per se as well as devices also known per se, intended more particularly for tensioning the ribbon and protecting this latter from dust.

In an advantageous embodiment of the storage and feeding device of the invention, it is further provided with a device for varying the feeding speed of the ribbon so as to vary in particular the thickness of said liquid reactive film so as to always completely fill the space formed between said shoulders of the ribbon and situated between jointing turns of the wound ribbon, depending on the thickness adopted for these shoulders.

In another advantageous embodiment of the storage and feeding device of the invention, it further comprises a horizontal plate, disposed between said two spools, which ensures the inherent flatness more especially of said micro-wells.

In yet another advantageous embodiment of the storage and feeding device of the invention, it comprises magnetic recording and reading heads in front in which said lateral magnetic tracks of the ribbon travel.

The present invention also provides a microscopic analysis device, more especially for biological samples fixed on the smooth ribbon in accordance with the invention, characterized in that it comprises two jaws, for clamping said ribbon therebetween, one jaw of which is fixed to a light condenser, whereas the other jaw is fixed to a micro-scopic lens aligned with a condenser, these two jaws each having a central opening for illuminating and observing the samples, respectively.

In an advantageous embodiment of the analysis device of the invention, in the case of dry observation, the two jaws are pivotably mounted about a hinge.

In another advantageous embodiment of the analysis device of the invention, in the case of liquid phase observation, namely with immersion, the jaw supporting the microscopic lens is fixed to the bottom of a cup containing the liquid in which the ribbon is immersed, whereas the jaw supporting the light condenser is separated from the jaw carrying the microscopic lens and fits, by a snap fit or other means, into this latter after receiving said ribbon.

The present invention further provides an apparatus for continuously supporting, treating, storing and analysing fixed or living biological samples carried by the ribbon according to any one of the preceding arrangements, wherein said cassette device for storing and feeding said ribbon cooperates with:

at least one device for distributing said biological samples on the smooth or micro-well ribbon, respectively;

at least one microscopic analysis device, more especially for fixed biological samples, in accordance with the preceding arrangements, or an optical analysis device for living biological samples, comprising more especially optical fibers;

at least one treatment tank known per se;

at least one image acquisition device, connected more especially to said microscope lens, known per se and formed in particular by a TV camera or a CCD array;

a microprocessor for controlling the different devices and for possible data processing.

In an advantageous embodiment of the apparatus of the invention, it comprises two microscopic analysis devices of the above type which are disposed in cascade and which have a power of resolution and/or a lighting power, identical or different, the first optical device allowing overall observation with low magnification and phase contrast, whereas the second optical device provides microscopic observation with high fluorescence magnification and different wave lengths.

In another advantageous embodiment of the apparatus of the invention, said microscopic analysis device slides laterally with respect to the supporting jaws under the action of a step by step motor for high resolution scanning across the width of the ribbon.

In yet another advantageous embodiment of the apparatus of the invention, the optical device comprises a microscopic observation lens with very large field and high resolution, which cooperates with a high performance camera.

In another advantageous embodiment of the apparatus of the invention, it comprises a plurality of cassette storage and feeding devices intended to be treated in parallel.

In yet another advantageous embodiment of the apparatus of the invention, said device for distributing biological samples in said micro-wells is of the dosage syringe type and is coupled to a step by step motor.

Besides the preceding arrangements, the invention comprises further arrangements which will be clear from the following description.

BRIEF DESCRIPTION OF THE DRAWINGS

The invention will be better understood from the complement of description which follows, with reference to the accompanying drawings in which.

It should of course be understood that these drawings and the corresponding descriptive parts are given solely by way of illustration of the object of the invention, of which they form in no wise a limitation.

DESCRIPTION OF THE PREFERRED EMBODIMENTS

It is indispensable not only for smears but also for histological sections which are intended for microscopic analysis, to have a carrier with good optical qualities, good rigidity and a refraction index close to the index of the tissues (between 1530 and 1570). There now exist polymers complying with these characteristics and very widely used as flexible slides for cell culture. They have the further advantage of being wettable, of having high adherence properties with respect to the cells, of withstanding solvents and dyeing products (except acetone-ether) and withstanding heating at a temperature higher than 100° C. So a smear may be obtained using the usual means, or histological sections may be deposited on such a carrier and an excellent spontaneous adherence obtained. If required, the carrier may be slightly heated or else a carrier may be used previously coated with a fine gelatine film or with a resin polymerizable by ultra violet radiation, as proposed by Technicon in its patent application filed in the United States of America under the No. 759 557.

The ribbon 1 of the invention has two longitudinally extending lateral data storage tracks 2 forming a shoulder which are made from a magnetic material for magnetic location, but which may be made from polymer like the carrier and formed as simple extra-thicknesses.

Figure 1:
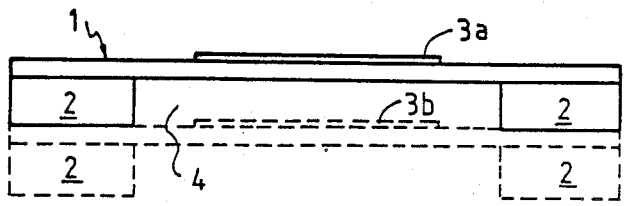
FIG. 1 shows a cross sectional view of the carrier ribbon for biological samples, more especially fixed, in accordance with the invention.

FIG. 1 shows in section the carrier with the transparent ribbon 1, the magnetic tracks 2 and a longitudinally extending biological storage zone, on a lateral section of the upper surface of ribbon 1, carrying a biological sample 3a. Underneath is shown with broken lines, also in section, a similar turn also comprising a carrier 1, the magnetic tracks 2 and another biological sample 3b. The space 4 thus formed between two turns, on the one hand, protects the samples and, on the other hand, behaves as a reservoir in which different substances may be placed, as will be seen further on.

Figure 2:
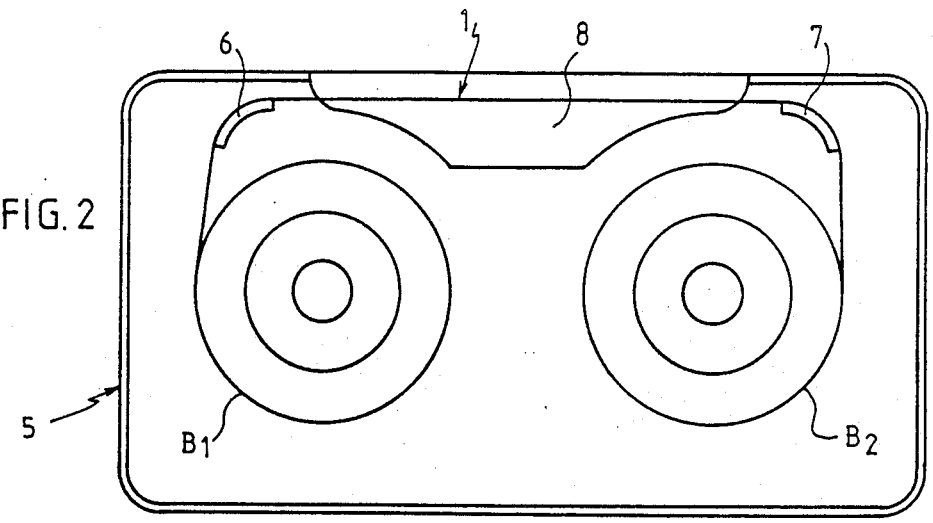
FIG. 2 shows schematically the ribbon storage and feeding device of the invention.

FIG. 2 shows a cassette 5 with two spools $B_1$ and $B_2$ having a nominal identical and relatively large diameter for providing a radius of curvature compatible with the relative rigidity of the carrier. Two shoes 6 and 7 guide the ribbon 1, in particular for tensioning it in space 8. In addition, this cassette 5 also comprises conventional devices used in video tape recording (and not shown) for maintaining the tension of the ribbon and for protecting it from dust.

By way of example, it should be pointed out that the capacity of a cassette with outer dimensions of 350 mm by 250 mm and containing spools having a diameter of 80 to 200 mm is about 6 m of ribbon of a thickness of 2 mm. The width is about 20 mm offering a useful surface of 10 mm. Thus, such a cassette may receive about 250 smears and 500 to 1000 histological sections depending on their size. Thus the space saved is of the order of 3 to 10 times with respect to slide boxes.

It should be noted that application on the ribbon of fixed (or non living) samples may be automated by using a microtome for the histological samples or a hematological spreading device for blood samples, of a type known to technicians in the matter.

The ribbon of the invention totally avoids the mounting of a slide because of an original optical immersion observation device which will now be described and which has the further advantage of preset focusing.

Figure 3:
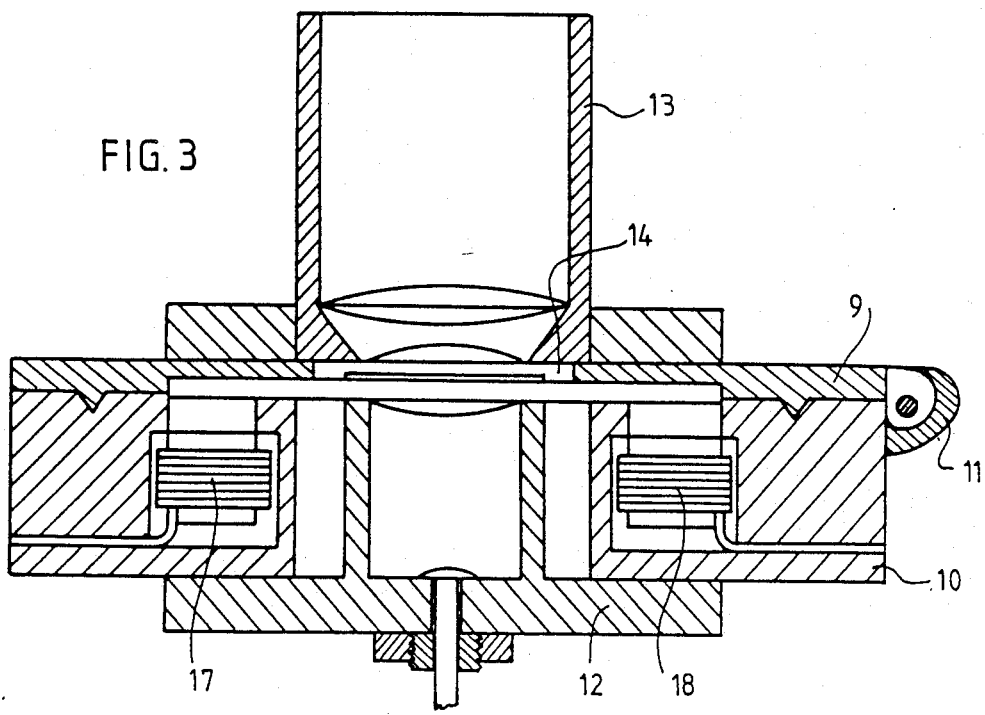
FIG. 3 shows a vertical section of the dry microscopic analysis device, in accordance with the invention, for the analysis of biological samples placed on the ribbon of FIG. 1 and cooperating with the device for storing and feeding this ribbon shown in FIG. 2.

As shown in FIG. 3, the carrier 1 is inserted between two jaws 9 and 10 which are pivotably mounted about a hinge 11 in the case of dry observation. Carrier 1 fits into grooves in these two jaws. Furthermore, carrier 1 slides over a light condenser 12 and is positioned with great accuracy opposite the lens 13 which is at a variable distance depending on the gauge chosen (between 1/10 mm and 1 mm). Thus a space 14 is provided (cf. FIG. 3) which may be empty for dry observation, but filled with a liquid for immersion analysis. In this latter case, the liquid may be simply water and in particular the water having served for the last rinsing of carrier 1 in a continuous dyeing operation. It may obviously be immersion oil or glycerine-containing water or any other transparent liquid having a refraction index compatible with the optical system used.

Figure 4:
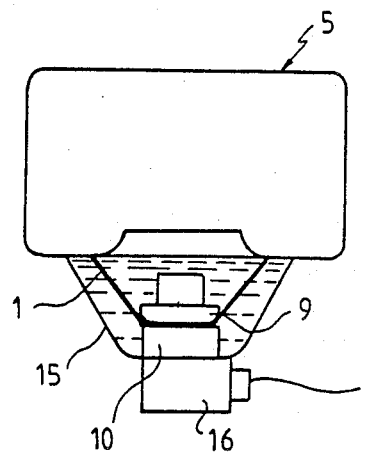
FIG. 4 shows a variant of the microscopic analysis device of FIG. 3 for liquid phase analysis.

FIG. 4 shows carrier 1 unwound and placed in piece 10 which carries the illumination system 12 (optical fiber system) of FIG. 3. Then a relative movement causes immersion in a tank 15 which comprises jaw 9 carrying the magnifying lens 13 which is connected to an image acquisition device 16, which may be optical for direct observation and/or electronic (TV camera or CCD). Here, in this liquid version, parts 9 and 10 are not mounted for pivoting as described above, but fit one in the other by a translational movement.

In a number of cases, more especially for hematology, it is not necessary to provide lateral movement of the optical devices for scanning a large surface. For other applications, in particular for histology, it is necessary to analyse a trace of a width going from several millimeters up to 1 cm.

Thus, this question may be solved with three types of solutions. First of all, it is easy to dispose several optical devices in series having different or identical power and/or illumination characteristics and, in this latter case, only the position of the optical axis varies thus doubling the scanned surface (for two devices). This is obviously a costly solution if the purpose is only to increase the analyzed surface. On the other hand, the series arrangement offers a very interesting possibility of very rapidly analyzing the same microscopic object according to different characteristics; for example, overall analysis with low magnification with phase contrast followed by an analysis with high fluorescence magnification at different wave lengths.

Another solution is to cause parts 12 and 13 of FIG. 3 to slide with respect to jaws 9 and 10 by means of a device driven by a stepper motor.

Finally, very wide field and high definition lenses may be used, which requires the use of a high performance camera. The choice between these three solutions will depend on the application contemplated and the device, such as it is designed, offers great versatility from this point of view.

One of the essential problems in automated cytological and histological diagnosis is that of being able to find the suspect information again very rapidly. The aim which we have set ourselves is to allow the specialist doctor to carry out very rapid daily checks. It will be remembered that a cassette may contain the equivalent of several hundred smears or biopsies and that it is thus possible to rerun the carrier and to stop at the zones which contain a remarkable event. For that the magnetic tracks 2 of carrier 1 travel past magnetic recording and reading heads 17 and 18.

The complete data processing sequence is as follows: at the outset, the cassette only comprises on the magnetic tracks the series number code, the carrier type code (for avoiding wrong use thereof) and the distance location code. When the cassette is loaded with biological samples, they are placed in zones predefined by the program depending on the size and nature of the sample. To each deposited sample will correspond, on a track, the sample code which identifies the subject and the rank (for example, number of the seriate section). The second track is for example reserved for the analysis and two types of information are progressively written therein: on the one hand, pulses for locating the positions of characteristic events and on the other the quantitative results of the analysis reinjected by a control microprocessor. It may be assumed that the mean analysis time per sample is of the order of a minute.

During the check, the very high speed run through may cause the suspect cells to appear at will whose rate of occurrence is as a rule of the order of a few per cent, which leads to an acceptable checking time.

Depending on the complexity of the analysis and on the results to be stored, the two lateral tracks may themselves be divided into several tracks reserved for different information.

Thus, the carrier serves both for collecting biological samples and analyzing them and also for storing information.

In this connection, it is interesting to note that it is possible to protect the information relating to certain particular biological samples, particularly biopsies or legal medicine preparations, against any indiscretion by data processing coding.

It should further be mentioned that the presence of later magnetic tracks allowing, among other things, coding and high accuracy location (of the order of 10 $\mu$m) avoids the need to use complex mechanical feeding and location devices.

Carrier 1, because of its special form, provides a space 4 between turns which may contain any liquid film. To grasp the significance of this possibility, let us consider the use of ribbon 1 of the invention in connection with liquid phase operations, such as dewaxing, fixing, dyeing operations and various biochemical reactions. Let us consider, in particular, the example comprising eight sequential operations: a fixing operation, lasting five minutes, three rinsing operations lasting two minutes each, a dyeing operation lasting ten minutes and three rinsing operations lasting two minutes. The carrier 1 is unwound, let us suppose in a minute, while passing through a fixing bath, is then rewound in a minute, and a liquid fixing film is formed in space 4 by capillarity. The carrier remains rolled up for three minutes then it is unrolled in the first rinsing bath, then rolled up again and so on. Thus, by alternating unwinding, immersion, then rewinding, a complete fixing/dyeing cycle on a carrier equivalent to 500 glass slides can be carried out in a time very little different from that required by a single slide. In addition, several cassettes may be treated in parallel in a machine of reduced size.

Finally, in some cases, when the throughput rates are very much reduced, the cassette may be used continuously in an apparatus in which the operations take place in the same tank while changing liquid, or directly on the support by spraying or by dripping, or else in successive tanks.

Protection of the samples is obtained by space 4. For filing, the samples may be kept either dry or in a neutral conservation liquid which may be the one which served for observation and rinsing purposes (glycerine-containing water, oil, etc ...). In some cases a transparent adhesive film or else flexible slides may be deposited.

The carrier of the invention can also be used for cell culture and more especially bacterial culture. The conditions to be complied with are very different from those corresponding to the analysis of cells and non living tissues. In this case, the essential requirements are:

liquid phase working in micro-wells;
non contamination;
reagents or substrates varying from one well to another;
storage from 12 to 24 hours at 37° C. for allowing bacterial proliferation;
optical analysis (turbidimetry, nephelometry, or colorimetric reaction).

The results obtained allow the bacteria to be identified, but also define the efficient antibiotics and the corresponding doses. In this respect, it should be mentioned that these manipulations are carried out at the present time in a multihole Petri box or in galleries containing the media and reagents in lyophilized form and require enormous staff, time and consumable product investments, which fully justifies an automated approach.

The modification of the basic carrier, as we have just described it, is conceivable in two different ways:

the creation of micro-wells directly in the carrier, or else,
fixing micro-wells on the carrier.

Figure 5A:
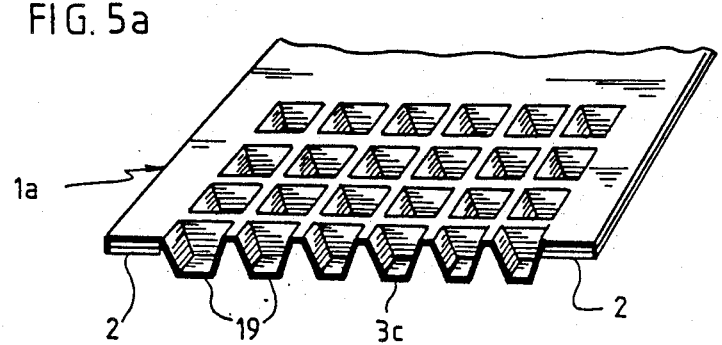
FIGS 5a and 5b show perspective views of another embodiment of the ribbon of the invention adapted for the analysis of living biological samples, more especially for bacteriological analysis.
Figure 5B:
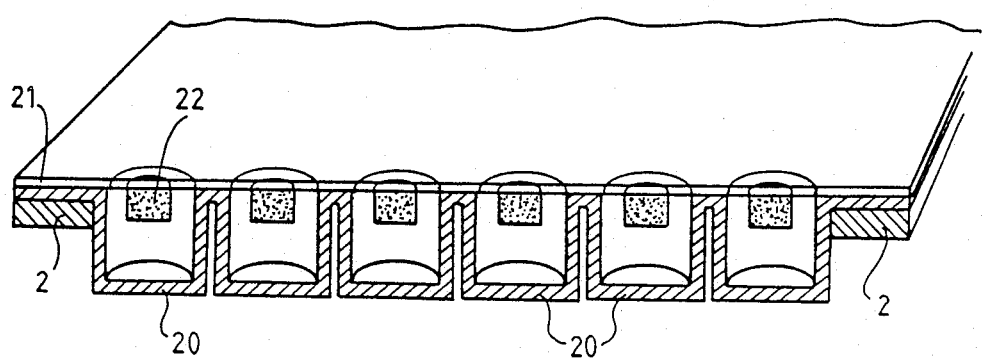

FIGS. 5a and 5b show two variants 1a and 1b of ribbon 1, with micro-wells which may be polyhedral 19, or cylindrical 20. It will be noted that the micro-wells are formed by molding in the ribbon and that this latter carries the two magnetic tracks 2 for locating and storing the results.

The micro-wells 20 of FIG. 5b may comprise an adherent lyophilized product, or this product may adhere to an adhesive protection film 21 in the form of pads 22 impregnated with lyophilized product, these pads being protected also by a protection skin (not shown) previously applied to film 21 and which is removed before use.

These pads 22 carry the lyophilzed substrates, dyes or similar.

A ribbon conforming to FIGS. 5a and 5b may be inserted in a storage and feeding cassette. This cassette causes ribbon 1a or 1b to advance row after row and the device for distributing cell samples in suspension (not shown), coupled possibly to a stepper motor, injects in each micro-well a small amount of the cellular suspension 3c to be analyzed.

For this, it will be noted that the cells may be collected automatically at the output of a cytofluorimeter for sorting the cells, known to technicians in the matter.

A plate, (not shown) disposed between the spools of the cassette ensures in this case the inherent flatness of ribbon 1a or 1b; the micro-wells are then covered with the adhesive film 21 which bears the small pads impregnated with lyophilized products. This adhesive film 21 ensures on the one hand sealing in any position of the filled wells, and also avoids contamination while allowing gas exchanges if the reactions are desired under aerobic conditions; for this, film 21 is permeable to air. It goes without saying that for reactions under anaerobic conditions, film 21 is impermeable to air. In any case, this film 21 is impermeable to the cellular suspension, which cannot flow even with the well in the reversed condition.

With a cassette capable of comprising several thousand micro-wells, it is also possible to test in parallel between 30 and 50 inocculates. The cassette is then placed in an incubator at 37° C. coupled to a reading device, particularly an optical fiber device, in which one optical fiber serves for the input whereas another optical fiber serves for collecting the light: this latter is advantageously reflected from the reflecting face (for example silver coated) of said lyophilized product pads. The measurement conditions may vary depending on the position of the micro-well and range from measurement under diffusion conditions up to the maximum of luminosity under reflection conditions.

The unwinding and rewinding of the carrier allows not only dynamic measurements to be carried out on the whole of the micro-wells of the ribbon, namely for checking how the reaction develops in time, at the level of each micro-well through repeated reciprocal movements, but also allows the agitation to be imparted to the cellular suspensions required for promoting the reactions. Withdrawal from said incubator takes place when the results acquired become significant.

Figure 6:
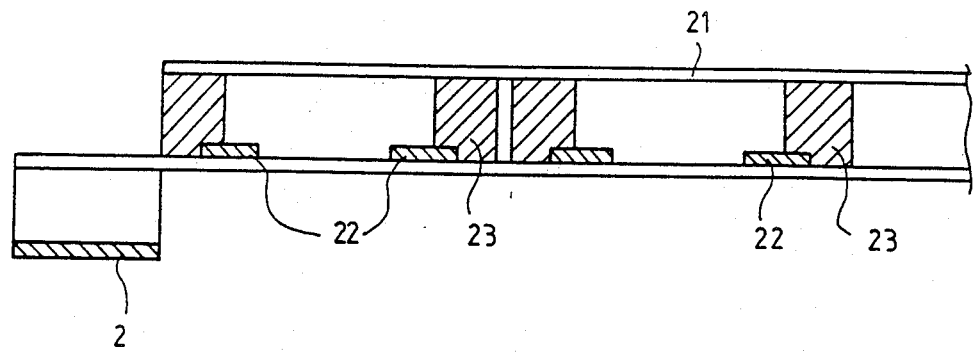
FIG. 6 shows the variant of the embodiment of FIGS. 5a and 5b.

So as not to modify the smooth ribbon 1, such as it was initially defined, the micro-wells may be created by fixing on the ribbon rings 23 which themselves contain pads 22 impregnated with lyophilized products (thus the ribbon 1c of FIG. 6). An adhesive 21 in this case also covers the micro-wells 23 after they have been filled. The height of the magnetic tracks 2 is increased so that space 4 may contain the micro-wells.

Figure 7:
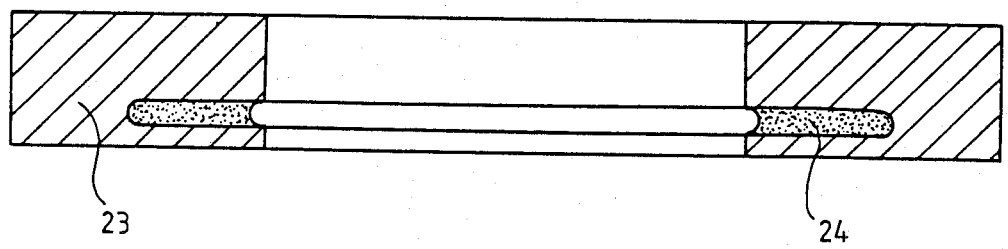
FIG. 7 shows a variant of the toroidal rings forming living sample carrier micro-wells with respect to the rings of FIG. 6.

In another variant, rings 23 have a groove 24 (cf. FIG. 7) which contains the lyophilized substance. During fixing of the adhesive film 21, crushing promotes release of the product and diffusion thereof in the micro-wells.

As is clear from the foregoing, the invention is in no way limited to those of its embodiments and modes of application which have been more explicitly described: it embraces on the contrary all variants thereof which may occur to a man skilled in the matter, without departing from the scope or spirit of the present invention.

What is claimed is:

1. A device for the automatable analysis of biological samples, comprising:
a flexible coiled, non-hydrophobic polymeric ribbon, said ribbon having two longitudinally extending laternal edges, a longitudinally extending biological storage zone for storing biological samples on a first lateral section of an upper surface of said ribbon, and a longitudinally extending first data storage zone longitudinally coextensive with said biological storage zone and made of a magnetic or optical data storage medium for storing said data specific to each biological sample to be stored on said biological storage zone, on a second lateral section of a longitudinal surface of said ribbon, said second lateral section being at a lateral edge of said ribbon and spatially distinct from said first lateral section, a longitudinally extending second data storage zone longitudinally coextensive with said biological storage zone and made of said data storage medium, for storing data specific to each biological sample to be stored on said biological storage zone, on a third lateral section of said ribbon at a laternal edge of said ribbon and spatially distinct from said first and second lateral sections, said biological storage zone being positioned centrally with respect to said lateral edges and between said first and second data storage zones wherein said data storage medium of both said first and second data storage zones is attached to a lower surface of said ribbon, opposite said upper surface, so that said first and second data storage zones form, respectively, first and second shoulders downwardly depending from each said lateral edge, so as to form a reservoir between adjacent turns of said coil and between said lateral shoulders, said shoulders contacting the upper surface of said ribbon at an adjacent lower turn of said coil, said data storage medium being capable of storing data indicating the longitudinal location of any biological sample stored on said biological storage zone.

2. The device of claim 1, wherein said data storage medium is magnetic.

3. The device of claim 1, wherein said ribbon is wound about a first spool.

4. A device for the automatable analysis of biological samples, comprising:
a flexible non-hydrophobic polymeric ribbon, said ribbon having two longitudinally extending lateral edges, a longitudinally extending biological storage zone for storing biological samples on a first lateral section of an upper surface of said ribbon, and a longitudinally extending first data storage zone longitudinally coextensive with said biological storage zone and made of a magnetic or optical data storage medium for storing data specific to each biological sample to be stored on said biological storage zone, on a second lateral section of a longitudinal surface of said ribbon, said second lateral section being at a lateral edge of said ribbon and spatially distinct from said first lateral section, a longitudinally extending second data storage zone longitudinally coextensive with said biological storage zone and made of said data storage medium, for storing data specific to each biological sample to be stored on said biological storage zone, on a third lateral section of said ribbon at a lateral edge of said ribbon and spatially distinct from said first and second lateral sections, said biological storage zone being positioned centrally with respect to said lateral edges and between said first and second data storage zones, said data storage medium of both said first and second data storage zones being attached to a lower surface of said ribbon, opposite said upper surface, so that said first and second data storage zones form, respectively, first and second shoulders downwardly depending from each said lateral edge, so as to form a reservoir therebetween; and an analysis means for microscopic analysis of biological samples, said analysis means including a light condenser and a microscopic lens, two jaws for clamping said ribbon therebetween, said two jaws having mutually aligned central openings, one of said jaws being secured to said light condenser, the other said jaw being secured to said microscopic lens, said light condenser and said microscopic lens being aligned with each other and said central openings.

5. The analysis device as claimed in claim 4, wherein the two jaws are pivotably mounted for rotation upon a hinge.

6. The analysis device as claimed in claim 4, wherein the jaw secured to the microscopic lens is fixed to a bottom of a tank containing a liquid, whereas the jaw secured to the light condenser is separated from the jaw carrying the micro-scopic lens and is adapted to be fitted, by a snap fit, in this latter after receiving said ribbon.

7. A device for the automatable analysis of biological samples, comprising:
a flexible non-hydrophobic polymeric ribbon, said ribbon having two longitudinally extending lateral edges, a longitudinally extending biological storage zone for storing biological samples on a first lateral section of an upper surface of said ribbon, and a longitudinally extending first data storage zone longitudinally coextensive with said biological storage zone and made of a magnetic or optical data storage medium for storing data specific to each biological sample to be stored on said biological storage zone, on a second lateral section of longitudinal surface of said ribbon, said second lateral section being at a lateral edge of said ribbon and spatially distinct from said first lateral section, a longitudinally extending second data storage zone longitudinally coextensive with said biological storage zone and made of said data storage medium, for storing data specific to each biological sample to be stored on said biological storage zone, on a third lateral section of said ribbon at a lateral edge of said ribbon and spatially distinct from said first and second lateral sections, said biological storage zone being positioned centrally with respect to said lateral edges and between said first and second data storage zone, said data storage medium of both said first and second data storage zones being attached to a lower surface of said ribbon, opposite said upper surface, so that said first and second data storage zones form, respectively, first and second shoulders downwardly depending from each said lateral edge, so as to form a reservoir therebetween, said ribbon being wound about a first spool which is rotatably mounted within a cassette protecting said ribbon from dust;
a second spool, to which an end of said ribbon is attached, spaced apart from said first spool and rotatably mounted within said cassette; and
tensioning means for providing tension to said ribbon, positioned between said first and second spools,
wherein said biological zone comprises a plurality of rows of polyhedral micro-wells integral with said ribbon and disposed perpendicularly to said upper and lower surfaces of said ribbon.

8. A device for the automatable analysis of a biological samples, comprising:
a flexible non-hydrophobic polymeric ribbon, said ribbon having two longitudinally extending lateral edges, a longitudinally extending biological storage zone for storing biological samples on a first lateral section of an upper surface of said ribbon, and a longitudinally extending first data storage zone longitudinally coextensive with said biological storage zone and made of a magnetic or optical data storage medium for storing data specific to each biological sample to be stored on said biological storage zone, on a second lateral section of longitudinal surface of said ribbon, said second lateral section being at a lateral edge of said ribbon and spatially distinct from said first lateral section, a longitudinally extending second data storage zone longitudinally coextensive with said biological storage zone and made of said data storage medium, for storing data specific to each biological sample to be stored on said biological storage zone, on a third lateral section of said ribbon at lateral edge of said ribbon and spatially distinct from said first and second lateral sections, said biological storage zone being positioned centrally with respect to said lateral edges and between said first and second data storage zones, said data storage medium or both said first and second data storage zones being attached to a lower surface of said ribbon, opposite said upper surface, so that said first and second data storage zones form, respectively, first and second shoulders downwardly depending from each said lateral edge, so as to form a reservoir therebetween, said ribbon being wound about a first spool rotatably mounted within a cassette protecting said ribbon from dust;
a second spool, to which an end of said ribbon is attached, spaced apart from said first spool and rotatably mounted within said cassette; and
tensioning means for providing tension to said ribbon, positioned between said first and second spools,
wherein said biological zone comprises a plurality of rows of cylindrical micro-wells integral with said ribbon and disposed perpendicularly to said upper and lower surfaces of said ribbon.

* * * * *